United States Patent [19]
Arlt et al.

[11] Patent Number: 4,874,473
[45] Date of Patent: Oct. 17, 1989

[54] SEPARATION OF DIASTEREOMERS BY EXTRACTIVE DISTILLATION

[75] Inventors: Dieter Arlt, Cologne; Ulrich Schwartz, Leverkusen; Hans-Walter Brandt; Wolfgang Arlt, both of Odenthal; Andreas Nickel, Wetter, all of Fed. Rep. of Germany

[73] Assignee: Bayer Aktiengesellschaft, Leverkusen, Fed. Rep. of Germany

[21] Appl. No.: 39,550

[22] Filed: Apr. 16, 1987

[30] Foreign Application Priority Data

Apr. 25, 1986 [DE] Fed. Rep. of Germany ....... 3613975

[51] Int. Cl.$^4$ .......................... B01D 3/40; C07B 57/00
[52] U.S. Cl. ............................................ 203/1; 203/3; 203/57; 203/58; 203/59; 203/60; 203/62; 203/63; 203/64; 203/65; 203/91; 560/57; 560/124; 562/402; 562/866; 562/856; 568/829
[58] Field of Search .................. 203/58, 57, 59, 60, 203/61–64, 50, 91, 1, 3; 560/57, 124; 568/829; 562/401, 402; 260/544 L

[56] References Cited

U.S. PATENT DOCUMENTS

| | | | |
|---|---|---|---|
| 3,491,152 | 1/1970 | Howard et al. | 568/340 |
| 3,847,755 | 11/1974 | Chanel et al. | 203/58 |
| 4,134,919 | 1/1979 | Yamanaka et al. | 568/829 |
| 4,196,304 | 4/1980 | Naumann | 560/124 |
| 4,306,077 | 12/1981 | Leigh | 562/402 |
| 4,488,937 | 12/1984 | Berg et al. | 203/58 |
| 4,599,444 | 7/1986 | Foggassy et al. | 562/402 |

FOREIGN PATENT DOCUMENTS

| | | |
|---|---|---|
| 2628477 | 12/1976 | Fed. Rep. of Germany ...... 562/401 |
| 7211139 | 11/1973 | France . |
| 1570557 | 7/1980 | United Kingdom . |

Primary Examiner—Wilbur Bascomb
Attorney, Agent, or Firm—Sprung Horn Kramer & Woods

[57] ABSTRACT

Diastereomers can be separated with good industrial success with the aid of extractive distillation. The separation process is characterized in that an auxiliary which changes the partial pressure of the various diastereomers to be separated to a different degree and thus allows easier separation of the diastereomers by distillation is added during the distillation. Using the present process diastereomic cis/trans-permetric acid methyl esters and mixtures of menthol and isomenthol can be separated with isolation of 99% pure product.

6 Claims, 2 Drawing Sheets

SEPARATION OF DIASTEREOMERS BY EXTRACTIVE DISTILLATION

The biological properties of chemical compounds are frequently linked to a particular steric structure of an active compound molecule. Efforts are therefore made for sterically uniform compounds which have a high biological action to be prepared or to be isolated from mixtures of the various stereoisomers. Because of the small (physical and/or chemical) differences in the properties of stereoisomers, this object can be achieved only with a great deal of effort. Processes known hitherto for separation of diastereomers are fractional crystallization and fractional distillation. Diastereomers are all the stereoisomers which are not enantiomers, that is to say do not behave as mirror images. The separation of diastereomers by fractional crystallization can of course be applied only to substances which are capable of crystallization and frequently leads to unsatisfactory yields. The separation of diastereomers by distillation can also be applied to liquids, but is frequently a complete failure. In the few cases which can be carried out in practice, an exceptionally high expenditure on apparatus is necessary because of the large number of separation stages required. Associated with this is a very expensive consumption of energy for the distillation. There was therefore an urgent need to find new and more practicable processes for the separation of diastereomers which do not have the disadvantages of the abovementioned separation processes.

It has now been found that diastereomers can be separated with good industrial success with the aid of extractive distillation. The separation process is characterized in that an auxiliary which changes the partial pressure of the various diastereomers to be separated to a different degree and thus allows easier separation of the diastereomers by distillation is added during the distillation.

Surprisingly, it is possible to separate diastereomers in a good space/time yield with substantially less expenditure on apparatus and energy with the aid of the extractive distillation. Separation preferably takes place here in fractionating columns, and preferably under reduced pressure, in particular under pressures of about $10^{-3}$ bar to about 1 bar.

The process according to the invention is in principle suitable for separation of all types of diastereomeric compounds which are stable under the extractive distillation conditions determined by the apparatus and auxiliary.

It is possible, for example, separate diastereomeric esters of α-(S)-methoxy-propionic acid and racemic α-phenyl-ethanol or racemic 1-chloro-3,3-dimethylbutan-3-ol into the diastereomers with the S,S- and S,R-configuration on the chiral centers by the process according to the invention. It is likewise possible separate amides of α-(S)-methoxy-propionic acid and racemic amines, such as, for example, the diastereomeric N-[1-(R,S)-phenyl-ethyl]-α-(S)-methoxy-propionic acid amides, into the individual stereoisomers by applying the extractive distillation.

Easy access to enantiomerically pure alcohols and amines, which can be prepared from the separated diastereomers by hydrolysis, thus results. Such products can be used as auxiliaries for the synthesis of pharmaceuticals, or are used as intermediate products for the preparation of high-grade plant protection agents.

The process according to the invention is preferably suitable for the separation of cyclic diastereomeric compounds, in particular carbocyclic and heterocyclic compounds containing 3 to 6 ring members. Diastereomeric compounds of the cyclopropane-cyclobutane and cyclohexane series are particularly preferably separated.

Examples which may be mentioned of diastereomeric cyclic compounds to separated according to the invention are:

From the cyclopropane series: cis- and trans-2,2-dimethyl-3-(methyl-1-propenyl)-1-cyclopropanecarboxylic acids or the cis- and trans-3-(2,2-dichlorovinyl)-2,2-dimethyl-1-cyclopropanecarboxylic acids, the acid chlorides of this acid or their methyl or ethyl esters and the acid chloride and the methyl and ethyl esters of 3-(2,2-dibromovinyl)-2,2-dimethyl-1-cyclopropanecarboxylic acid. The methyl esters of cis- and trans-caronaldehyde acid and the dimethyl acetal of these esters, as well as cis- and trans-2,2-dimethyl-3-(2,2,2-trichloroethyl)-1-cyclopropanecarboxylic acid chloride and 2,2-dimethyl-3-(4-chlorophenyl)-cyclopropane-1-carboxylic acid chloride and 3-(2-chloro-3,3,3-trifluoro-1-propenyl)-2,2-dimethylcyclopropane-1-carboxylic acid chloride may furthermore be mentioned.

Examples which may be mentioned from the cyclobutane series are cis- and trans-cyclobutane-1,2-dicarboxylic acid dinitrile and the diastereomeric 2-chloro-3,3-dimethyl-4-trichloroethylcyclobutanones.

Examples which may be mentioned from the cyclohexane series are the diastereomeric 2-isopropyl-5-methylcyclohexanols methanol, isomenthol, neomenthanol and neoisomenthol, and cis- and trans-2-tert.-butylcyclohexyl acetate and cis- and trans-4-tert.-butylcyclohexyl acetate.

Examples of heterocyclic compounds which may be mentioned are cis- and trans-2,6-dimethyl-morpholine and cis- and trans-N-(m-trifluoro-methylphenyl)-3-chloro-4-chloromethyl-pyrrolid-2-one.

The examples mentioned show the diversity of the new separation process. Certain stereoisomers of the compounds mentioned have advantageous properties in comparison with their epimers, that is to say certain derivatives of the cyclopropane and cyclobutane compounds mentioned are highly active insecticides in certain cases only in the form of the cis-compounds and in other cases in the trans-series.

The separation of the cyclohexane compounds mentioned leads to certain diastereomers which are useful aroma and flavour substances.

The heterocyclic compounds mentioned are examples of compounds which, in the form of a certain diastereomer, lead to highly active fungicides or have a particularly high herbicidal activity.

Possible auxiliaries to be added during the extractive distillation for simplification of the separation are, preferably, polar substances which have a boiling range from about 50° C. to about 310° C.

Possible suitable auxiliaries are, preferably, amines, ethers, amides, ketones, alcohols, nitriles, heterocyclic compounds and sulphones.

Examples which may be mentioned of suitable substances are: glycerol, diethanolamine, diphenyl ether, acetamide, N-methylacetamide, N-methylformamide, acetone, furfurol, acetonitrile, dimethylformamide, dimethylacetamide, N-methylpyrrolidone, N-formylmorpholine, benzyl alcohol, phenol, dimethylsulphoxide, sulpholane, glutaric acid dinitrile, succinic acid dinitrile, succinic acid amide, 1-methyloxo-phospholine and N- methylcaprolactam. In particular, sulpholane, 4-methylmorpholine, methylformamide, 2-pyrrolidone, N-methylacetamide, glutaric acid dinitrile, succinic acid dinitrile, succinic acid amide and 1-methyl-oxo-phospholine are in many cases advantageously employed according to the invention as the auxiliary.

The auxiliaries to be added allow or improve the separation of a given diastereomer mixture by distillation, in that they modify the interactions of the molecules present in the mixture such that one or more types of molecule undergo a change in the interaction energy by the presence of the auxiliary, this leading to one or more types of molecule now being more volatile than the others.

The choice of the auxiliaries to be employed for the separation is preferably made via the determination method of head space analysis. In this method, the substance mixture (diastereomer mixture) to be separated is introduced into a thermostatically controlled vessel and the composition of the resulting vapor phase is determined analytically by gas chromatography.

The separation factor can be determined accurately from the amounts of liquid weighed in reduced by the resulting amount of vapour, and the analytically determined vapour concentration. To determine the influence of the auxiliaries according to the invention, these are introduced into the thermostatically controlled vessels together with the substance mixture to be resolved. The separation factor is determined as already described. The preselection of the auxiliaries found according to the invention depends on their boiling point, which should be higher than that of the substance mixture to be separated the miscibility with the substance mixture to be separated and its ability to be distilled without undesirable decomposition occurring.

The separation factor is a measure of the possibility of separating diastereomer mixture by distillation.

A separation factor of one means that a mixture cannot be separated distillation, and values greater than one means an increasing ability to be separated.

The separation factor is determined, for example, via the vapor analysis described above. Other characteristics for distillative separation are the number of separation stages and the reflux ratio, which are to be defined briefly below.

Number of separation stages: The number of separation stages is the number of countercurrent exchange units in a distillation column. These correspond to the trays of a tray column or a certain packing height in columns with packing.

Reflux ratio: The reflux ratio indicates the distribution of the stream of material obtained in the condenser. It is the quotient of the stream flowing back into the column and the stream removed. Small values for the reflux ratio means a smaller consumption of energy, and large values means a high consumption of energy per kg of distillate generated.

Figure 1:
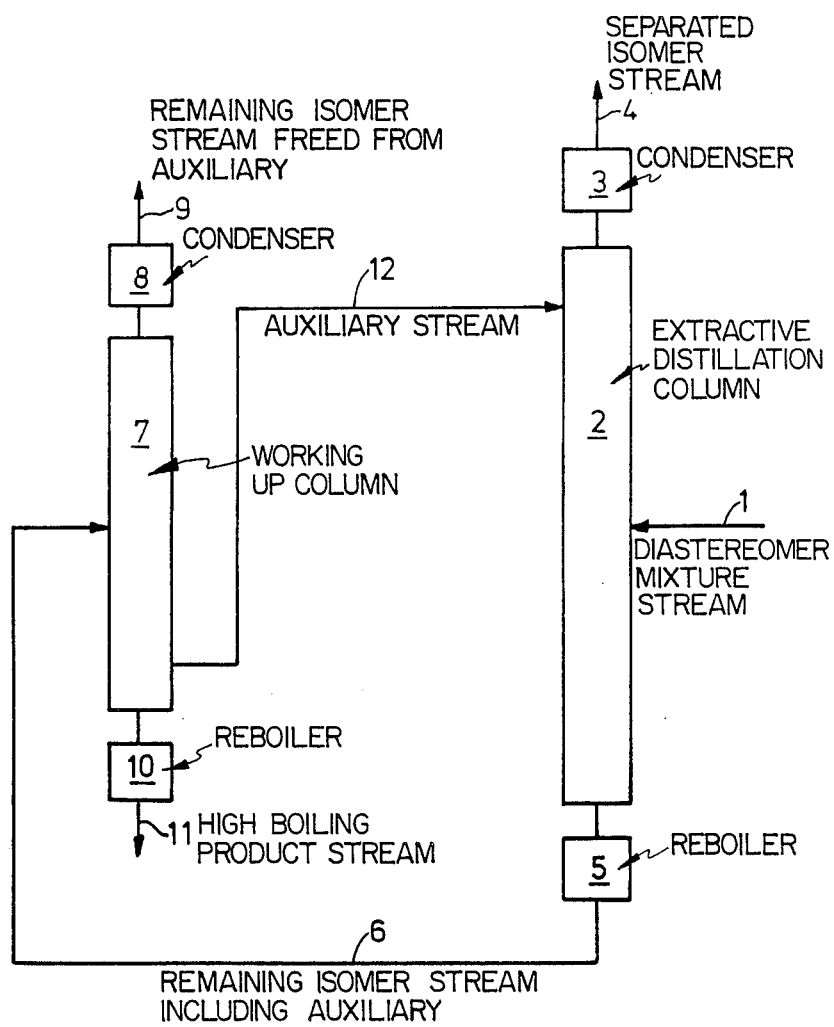
FIG. 1 is a schematic flow diagram showing an extractive distillation system suitable for the process according to the invention.

DETAILED DESCRIPTION OF THE INVENTION 2 is the extractive distillation column with its condenser 3 and the reboiler 5. The diastereomer mixture to be separated according to the invention, consisting of at least two isomers, flows into this column with stream 1. Stream 12 is the auxiliary employed in the process according to the invention, which effects separation of the mixture running in with 1. Stream 4 is one or more isomers separated from the feed mixture. The isomers which remain flow with stream 6 into the working up column 7 with its reboiler 10 and the condenser 8. The isomer or isomers which remain, freed from the auxiliary, are removed from the column with stream 9. The purified auxiliary flows back into the extractive distillation column 2 with stream 12. High-boiling products-formed by decomposition by heat or by other means are removed with stream 11.

The surprising superiority of the process according to the invention for the separation of diastereomeric compounds in comparison with distillative separation by fractional distillation without an auxiliary is shown by the following examples and comparison examples, where it should be taken into consideration that in many cases separation by simple fractional distillation fails.

EXAMPLE 1

Separation of cis/trans permethric acid methyl ester (3-(2,2-dichlorovinyl)-2,2-dimethyl-cyclopropanecarboxylate Given: Mixture containing 60% of cis-isomer and 40% of trans-isomer Aim: 99% isomer purity in the product streams 4 and 9 in FIG. 1.

The separation was carried out in accordance with the principle of FIG. 1. The exact experimental procedure can be seen from FIG. 2, the hourly streams of material and the experimental conditions being given.

Figure 2:
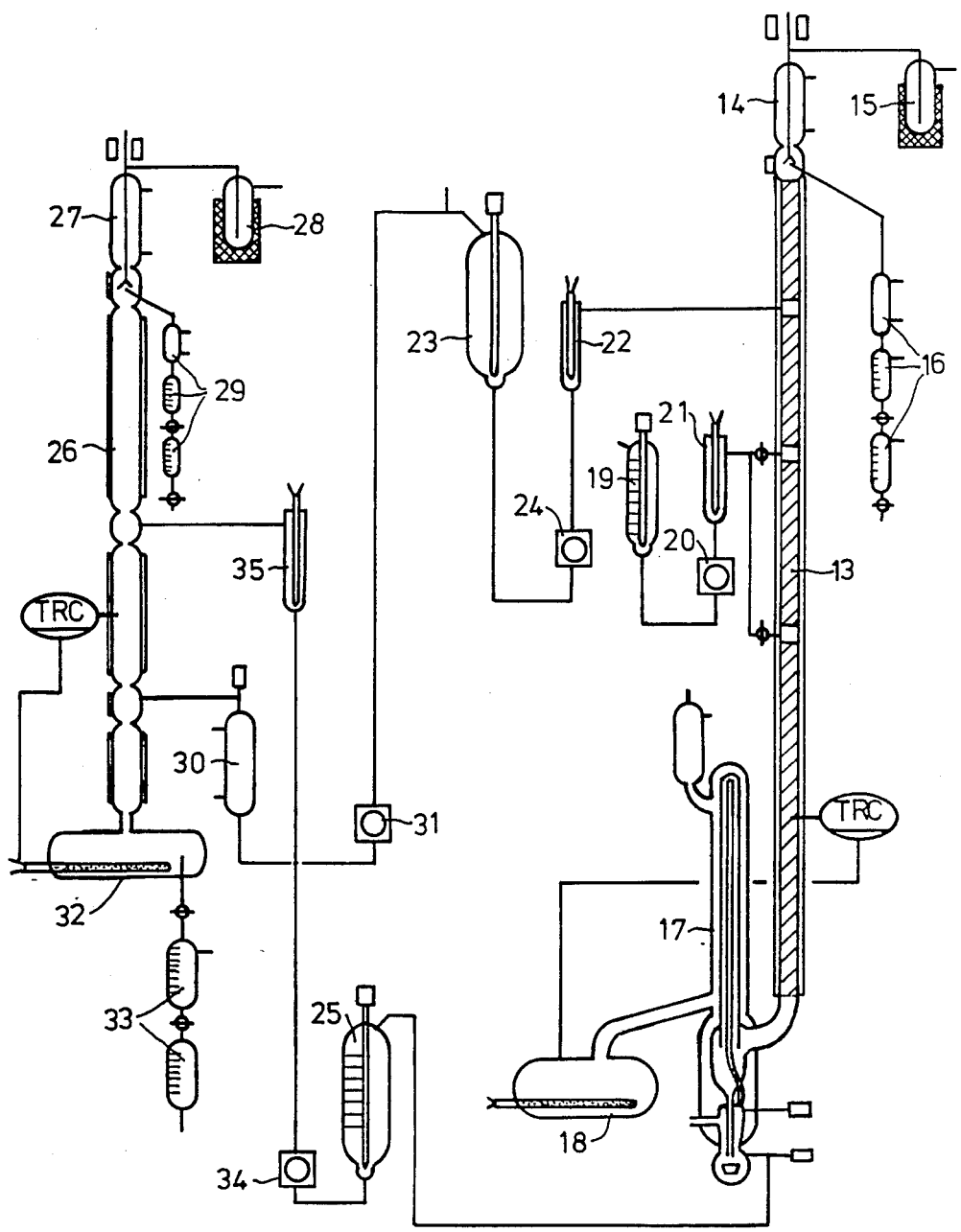
FIG. 2 is a schematic diagram illustrating equipment suitable for the experimental procedure according to the invention.

In FIG. 2, the numbers have the following meanings:

| | |
|---|---|
| 13 | Extractive distillation column |
| 14 | Condenser |
| 15 | Cold trap |
| 16 | Distillate receiver |
| 17 | Reboiler |
| 18 | Boiling thermostat |
| 19 | Isomer mixture receiver |
| 25 | Bottom product receiver |
| 21/22 | Feed preheater |
| 23 | Sulpholane receiver |
| 20/24 | Feed pumps |
| 26 | Solvent removal column |
| 27 | Condenser |
| 28 | Cold trap |
| 29 | Distillate receiver |
| 30 | Lateral stream condenser |
| 31 | Lateral stream pump |
| 32 | Reboiler |
| 33 | Bottom product receiver |
| 34 | Feed pump |
| 35 | Feed preheater |

Sulpholane (tetramethylene sulphone) is employed here as the auxiliary for separation of the two diastereomers.

Working up of cis/trans permethric acid methyl ester (=PAME) with sulpholane: operating conditions and hourly balance.

Extractive distillation column (13): 13.5 m (Sulzer BX DN 70)
Temperature in the lower region of (13): 165° C.
Pressure in the lower region of (13): 50 mbar
Temperature in the middle region of (13): 140° C.
Temperature in the condenser (14): 114° C.
Pressure in the condenser (14): 30 mbar
Amount of reflux to amount withdrawn (=R/W) in the condenser (14)=3:1.

A mixture of 243.4 g of cis-PAME, 0.5 g of trans-PAME and 5.0 g of sulpholane is obtained in the distillate receiver (16), a mixture consisting of 247 g of cis-PAME and 228 g of trans-PAME having been introduced into the isomer mixture receiver (19). A mixture of 3.6 g of cis-PAME, 227.5 g of trans-PAME and 2.0 g of sulpholane is obtained in the distillate receiver (29). 3,400 g of sulpholane per hour are added from the sulpholane receiver (23).

The temperature is 187° C. in the boiling thermostat (18), about 175° C. in the evaporator (32), 170° C. in the solvent removal column (26) (4×4 wire mesh rings, DN 50, 2×2,000 mm) and 117° C. in the condenser (27).

The pressure is 45 mbar in the evaporator (32) and 30 mbar in the condenser (27). The reflux ratio R/W in the condenser (27) is 1.5.

No high-boiling substances are obtained in the bottom product receiver (33). Vacuum is applied in the apparatus at the following points: cold trap (15), evaporator (17) and cold trap (28).

TRC in FIG. 2 denotes temperature recorder control.

| Result | without auxiliary | with the auxiliary sulpholane |
|---|---|---|
| Separation factor | 1.15 | 1.74 |
| Number of stages | 150 | 25 |
| Reflux ratio | 12 | 4 |

The example thus shows that it was possible to reduce the number of separation stages required from 150 to 25 and the reflux ratio from 12 to 4. It was possible to isolate in each case 99% pure cis- and trans-isomer.

EXAMPLE 2

Separation of cis/trans-permethric acid methyl ester

Instead of sulpholane, the following auxiliaries can also be used for the separation of the two diastereomers in accordance with the arrangement of Example 1: 4-methylmorpholine, methylformamide, 2-pyrrolidone, N-methylacetamide and 1-methyl-oxo-phospholine.

EXAMPLE 3

Separation of menthol/iso-menthol

Menthol/iso-menthol can be successfully resolved in accordance with the experimental arrangement of Example 1 using succinic acid diamide as the auxiliary.

| Result | without auxiliary | with succinic acid diamide |
|---|---|---|
| Resolution factor | 1.09 | 1.44 |
| Number of stages | 194 | 31 |
| Reflux ratio | 19 | 5 |

Conditions: 50/50 feed, 1% of highly volatile substances in the bottom product, 10% of substances of low volatility in the top product The following auxiliaries, for example, can furthermore be employed for the menthol/iso-menthol separation glutaric acid dinitrile, succinic acid dinitrile, camphor and malonic acid dinitrile.

What is claimed is:

1. A process for the separation of diastereomers from each other wherein said diastereomers are selected from the group consisting of cis/trans permethric acid esters, cis/trans acid chlorides of permethric acid, menthol/isomenthol and the methyl esters of cis/trans caronaldehyde acid comprising adding to a mixture of diastereomers an auxiliary which allows or improves the resolution of said diasteromer mixture by distillation and separating the diasteromers by extractive distillation said auxiliary being selected from the group consisting of glycerol, diethanolamine, diphenyl ether, acetamide, N-methylacetamide, N-methylformamide, acetone, furfurol, acetonitrile, dimethylformamide, dimethylacetamide, N-methylpyrrolidone, N-formylmorpholine, benzyl alcohol, phenol, dimethylsulphoxide, sulpholane, glutaric acid dinitrile, succinic acid dinitrile, succinic acid amide, N-methylcaprolactam, 4-methylmorpholine, 2-pyrrolidone and 1-methyl-oxo-phospholine.

2. A process according to claim 1, comprising carrying out said distillation using one or more fractionating columns under pressures of about 1 bar to about 1 mbar.

3. A process according to claim 1, wherein the auxiliaries to be employed for the separation of the diastereomers is selected in a preliminary experiment using head space analysis said preliminary experiment comprising
   (1) placing a portion of said diastereomer mixture in a thermostatically controlled vessel and determining the composition of the vapor phase produced analytically by gas chromatography
   (2) adding to another portion of the diastereomer mixture a portion of auxiliary, placing said mixture in a thermostatically controlled vessel and determining the composition of the vapor phase produced analytically by gas chromatography
   (3) determining the separation factor in each of the above from the amount of liquid weighed in reduced by the resulting amount of vapor and the analytically determined vapor concentration.

4. A process according to claim 1, comprising employing sulpholane as the auxiliary for the separation of diastereomeric cis/trans permethric acid methyl esters.

5. A process according to claim 1, comprising employing succinic acid diamide as the auxiliary for separation of the diastereomers.

6. A process according to claim 1, comprising carrying out the separation under reduced pressure.

* * * * *